(12) United States Patent
Ishida et al.

(10) Patent No.: US 6,719,184 B2
(45) Date of Patent: Apr. 13, 2004

(54) NONDESTRUCTIVE INSPECTION METHOD

(75) Inventors: Ryooji Ishida, Yamaguchi (JP);
Masakuni Ezumi, Houfu (JP);
Tsuyoshi Fujii, Kudamatsu (JP);
Masami Ogata, Kudamatsu (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/061,192

(22) Filed: Feb. 4, 2002

(65) Prior Publication Data
US 2003/0057258 A1 Mar. 27, 2003

(30) Foreign Application Priority Data

Sep. 25, 2001 (JP) .......................... 2001-290668

(51) Int. Cl.[7] .................. B23K 31/02; B23K 37/00; B23K 31/12
(52) U.S. Cl. .............. 228/112.1; 228/2.1; 228/102; 228/103; 228/104
(58) Field of Search ............... 228/2.1, 112.1, 228/114.5, 102, 103, 104; 73/801

(56) References Cited

U.S. PATENT DOCUMENTS

| 4,682,397 | A | * | 7/1987 | Harth et al. ........... 29/890.031 |
| 5,115,136 | A | * | 5/1992 | Tomasch ................. 250/461.1 |
| 5,519,182 | A | * | 5/1996 | Linzell .................... 219/117.1 |
| 5,611,479 | A | * | 3/1997 | Rosen ..................... 228/112.1 |
| 5,794,835 | A | * | 8/1998 | Colligan et al. ............. 228/2.1 |
| 5,902,935 | A | * | 5/1999 | Georgeson et al. .......... 73/801 |
| 6,102,636 | A | * | 8/2000 | Geise ........................ 409/231 |
| 6,422,449 | B1 | * | 7/2002 | Ezumi et al. ............ 228/114.5 |
| 6,460,752 | B1 | * | 10/2002 | Waldron et al. ........ 228/112.1 |
| 6,476,344 | B1 | * | 11/2002 | Fields et al. .......... 219/121.63 |
| 2002/0064250 | A1 | * | 5/2002 | Kurosawa et al. .......... 376/260 |
| 2002/0158626 | A1 | * | 10/2002 | Shay et al. ............ 324/207.16 |

FOREIGN PATENT DOCUMENTS

JP      02-290632 A    * 11/1990

* cited by examiner

*Primary Examiner*—L. Edmondson
(74) *Attorney, Agent, or Firm*—Antonelli, Terry, Stout & Kraus, LLP

(57) ABSTRACT

A rotary tool (140) is relatively moved against members (30, 30) to be welded so as to perform friction stir welding of said members, while blades (145) mounted on the rotary tool (140) and a rotary brush (220) are used to cut the welded portion, and swarfs on the cut surface are removed through a suction opening (225), before medium liquid is supplied on said cut surface through a supply opening (240). Next, an inspection roller (250) is rotated on the surface of the welded portion for inspection. A probe (251) is provided within the roller (250). Upon detecting a defect, paint is applied to the position of defect by a marking device (270). Thereafter, based on said marking, the joint portion is cut and repaired by welding.

16 Claims, 4 Drawing Sheets

NONDESTRUCTIVE INSPECTION METHOD

FIELD OF THE INVENTION

The present invention relates to a method for nondestructively inspecting the joint portion of members being welded by friction stir welding and the like, and the present nondestructive inspection is especially preferably applied to inspecting friction-stir-welded areas of aluminum alloy members used for example to construct railway cars and buildings.

DESCRIPTION OF THE RELATED ART

Friction stir welding is a method performed by inserting a rotating round shaft (called a rotary tool) to the members to be welded and moving the same along the joint line, thereby heating, softening, plasticizing and solid-phase welding the joint portion. The rotary tool comprises a large-diameter portion and a small-diameter portion. Upon welding, the small-diameter portion is inserted to the members, and the end surface of the large-diameter portion comes into contact with the welded members. A projection is provided to the joint portion in advance, which functions as the filler material for filling the gap that may exist between the two members. The central axis of the rotary tool is somewhat tilted. A cutting blade can be equipped to the large-diameter portion of the rotary tool for welding and cutting the projections simultaneously. Air is blown to remove the swarf from the upper surface of the projection. This method is disclosed in Japanese Patent Laid-Open Publication No. 2001-47262 (EP 1057575 A2).

SUMMARY OF THE INVENTION

When members are welded by an ordinary welding method, a void may be created at the joint region. However, since this void is generally spherical, it does not seriously affect the strength of the welded portion.

In case of friction stir welding, however, the defect is not spherical. If defect occurs, it is often continuous. In such case, it seriously defects the strength of the welded members.

In general, a nondestructive inspection is performed by manually sliding a probe generating ultrasonic wave along the joint portion, which requires much experience and skill.

Moreover, weld flash is formed on both sides of the weld portion by the friction stir welding. A semicircular pattern is created on the surface of the joint portion, which also causes flash. Therefore, it is difficult to inspect the welded members from the surface of the joint region. Even further, a semicircular recess or groove is formed on the surface of the joint region, which also makes inspection difficult.

Therefore, after completing the friction stir welding, it is possible to remove the flash and other unevenness by a separate cutting process and the like, and then perform the inspection. However, such method takes time and is costly.

The first object of the present invention is to automate the nondestructive inspection procedure of the friction stir welding portion.

The second object of the present invention is to reduce the cost for inspecting the welding portion.

The first object of the present invention is achieved by relatively moving a rotary tool against the members to be welded and friction stir welding said members, cutting a part of the welded portion at the same time, and performing a nondestructive inspection at a rear position therefrom.

The second object of the present invention is achieved by cutting a part of the welded portion and performing a nondestructive inspection at a rear position therefrom.

DETAILED DESCRIPTION OF THE PREFERRED EMBODIMENT

Figure 1:
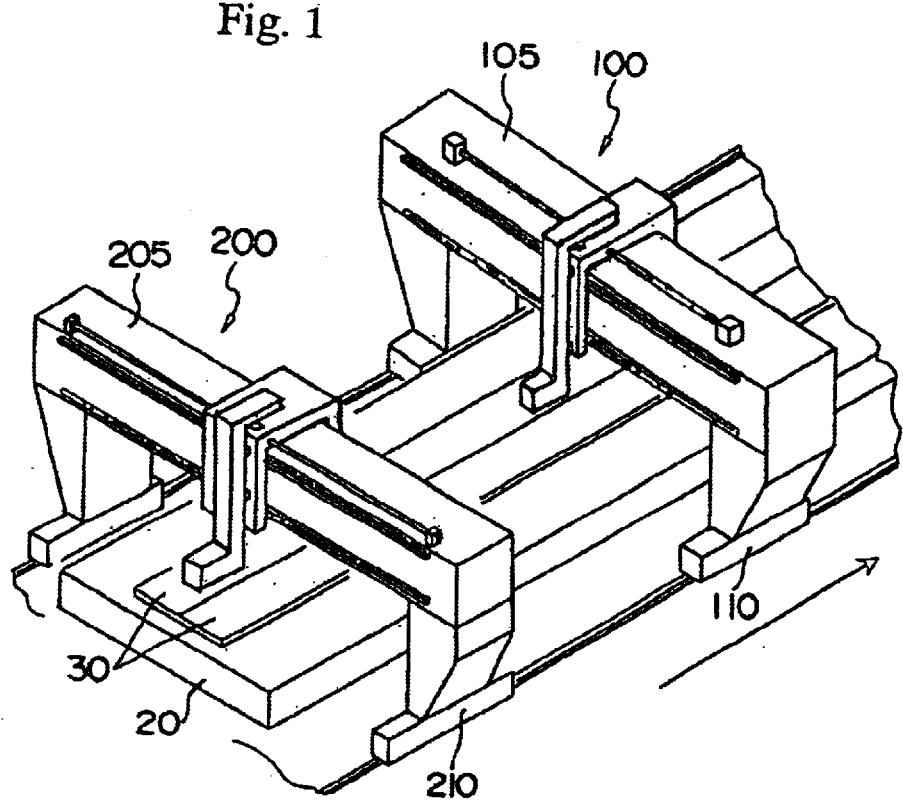
FIG. 1 is a perspective view of the device for welding and inspecting members according to one embodiment of the present invention.
Figure 2:
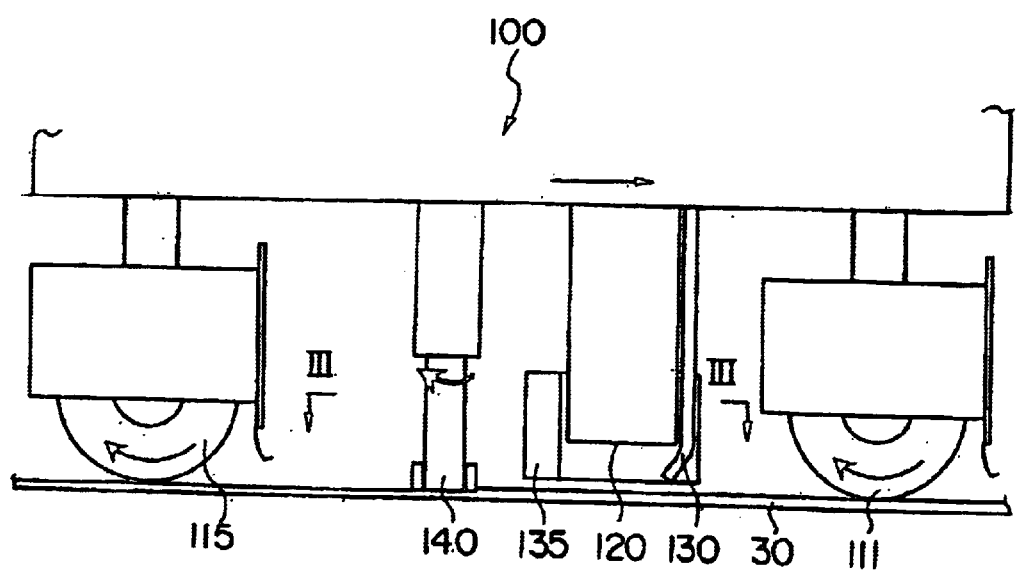
FIG. 2 is a side view of the welding device of FIG. 1.
Figure 3:
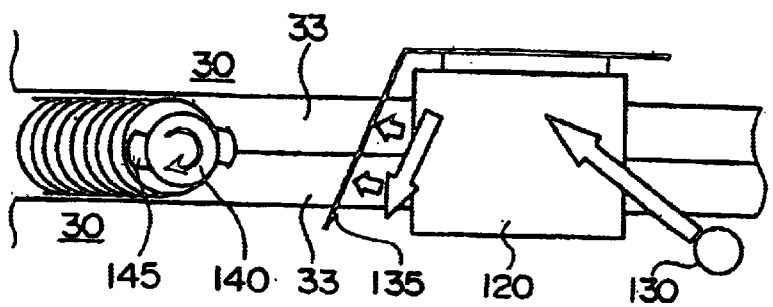
FIG. 3 is a cross-sectional view at line III—III of FIG. 2.
Figure 4:
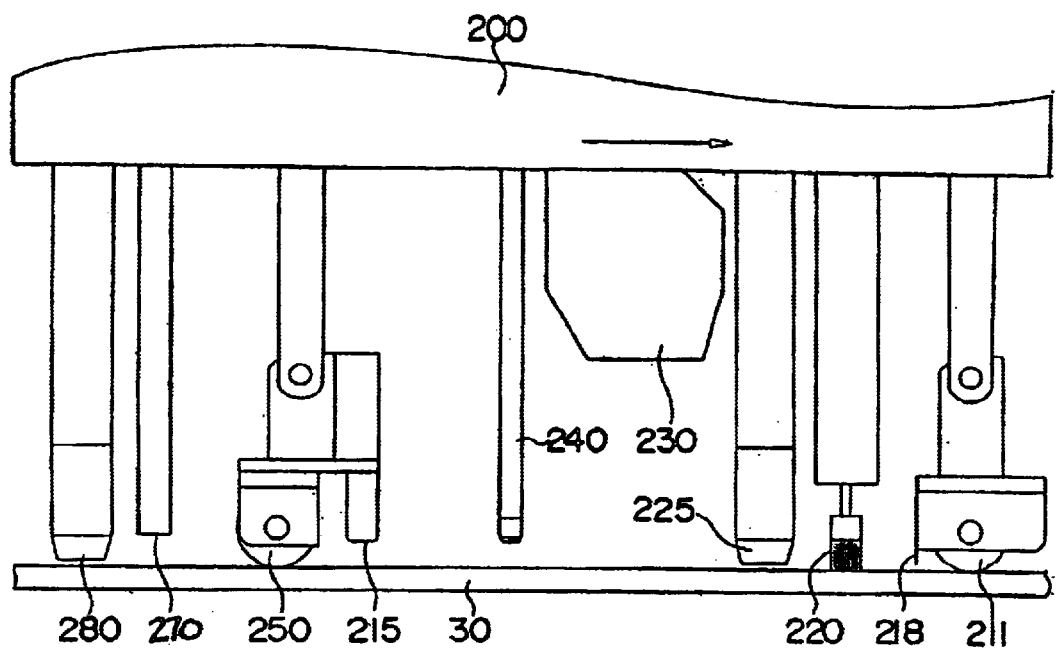
FIG. 4 is a side view showing the inspection device of FIG. 1.

A preferred embodiment of the present invention will now be explained with reference to FIGS. 1 through 8. In FIGS. 1, 2, 3 and 4, the device runs toward the right-hand side.

A pair of members 30, 30 to be welded are fixed to the upper surface of a bed 20. The abutted portions of the pair of members are friction-stir-welded. A friction stir welding device 100 and a nondestructive inspection device 200 are mounted on traveling members 110 and 210 that cross over and run along the bed 20. The devices 100 and 200 can travel along the beams 105 and 205 of the traveling members. Further, the rotary tool or the inspection device and the like of the devices 100, 200 can move up and down against the beams 105, 205. The nondestructive inspection device 200 is positioned so as to follow the friction stir welding device 100 in the friction stir welding direction.

Members 30, 30 are protruded members, each having a projection 33 at the end of a plate 31. The projections 33, 33 are protruded toward the upper direction. The members are fixed to the bed 20 with the ends having the projections 33 abutted against one another. Preferably, no gap is formed at the abutted region.

The friction stir welding device 100 comprises, from the front end of the friction-stir-welding direction in the following order, a holding roller 111, an optical sensor 120, an air blowout opening 130, a shield plate 135, a rotary tool 140, a holding roller 115, and so on. The holding rollers 111 and 115 press down and hold the two projections 33 and 33. The rollers 111 and 115 are supported elastically so as to press and hold the projections with predetermined force.

The optical sensor 120 detects the position of the width of projections 33, 33 or the position of the abutted portion, and guides the rotary tool 140 so that the central axis of the rotary tool 140 is disposed at the abutted portion. Moreover, the sensor detects the position of the upper surface of the projections 33 or the position of the upper surface of the plate 31 close to the projections, so that the rotary tool 140 is inserted to a predetermined depth at the abutted portion.

The rotary tool 140 comprises a large-diameter portion 141, a small-diameter portion 142 positioned at the tip (lower end) of portion 141, and plural blades 145 mounted to the outer periphery of the large-diameter portion 141 at the lower end thereof. The diameter of the large-diameter portion 141 is smaller than the total width of the two projections. The maximum diameter of the cut performed by the blades 145 is greater than the total width of the two projections 33, 33. The major cutting edge of each blade 145 is at its bottom surface. The small-diameter portion 142 is an external screw. The surface of the large-diameter portion 141 positioned at the border between the large-diameter portion and the small-diameter portion is concaved toward the large-diameter portion side.

During friction stir welding, the central axis of the rotary tool 140 is tilted toward the welding direction. It is tilted so that the tip of the small-diameter portion 142 precedes the large-diameter portion 141. During such state, the lowermost end of the large-diameter portion 141 is disposed between the line extending from the upper surface of the plate 31 and the apex of the projections 33. The position of the lowermost end of the large-diameter portion 141 becomes the position of the welding portion surface. The lowermost end of the blades 145 is disposed between the upper surface of the plate 31 and the upper surface of the welded portion.

When the friction stir welding device 100 is operated, the abutted members are friction-stir-welded, and the upper surface of the projections 33, 33 is recessed. A metal weld flash is created between the outer periphery of the large-diameter portion 141 and the projections 33, 33. The blades 145 cut off the projections 33, 33 that are disposed above the lower surface of the blades. Thereby, the weld flash and the projections 33, 33 that are disposed above the blades 145 are removed. As a result, the upper surface of the projections 33, 33 is cut to form an arced recess.

The swarf generated during the cutting process by the blades 145 is shielded from moving toward the optical sensor 120 and the holding roller 111 by the shielding plate 135 and the air discharged from the air blowout opening 130. When seen from above, the shielding plate 135 is L-shaped, and the block arranged along the traveling direction is fixed to the side surface of the optical sensor 120. The block disposed between the rotary tool 140 and the optical sensor 120 is slanted against the traveling direction. The air discharged from the air blowout opening 130 is blown towards the block of the shielding plate 135 arranged along the traveling direction, and then flows outward along the slanted block. Thereby, the swarf entering the optical sensor 120 side from under the block is blown aside. Further, air flows out through the space under the shielding block toward the rotary tool 140, preventing the swarf from entering therefrom.

The nondestructive inspection device 200 is positioned rearward in the welding direction from the friction stir welding device 100. The nondestructive inspection device 200 comprises, from the front end of the friction stir welding direction in the following order, a holding roller 211, a shielding plate 218, a rotary brush 220 that contacts the upper surface of the projections, a suction opening 225 for the swarf, an optical sensor 230, a medium fluid application opening 240, a holding roller 215, a nondestructive inspection roller 250, a marking device 270, a medium fluid suction opening 280, and so on. The rollers 211, 215 and 250 are supported elastically so as to press and hold the projections 33, 33 with predetermined force.

The rotary brush 220 is for cutting and removing the small flash generated by the cutting process using the blades 145, and is rotated by a motor. The rotary axis of the rotary brush 220 is disposed perpendicularly. The brush 220 also removes as much as possible the semicircular pattern created on the cut surface. The rotary brush removes the flash and the like from the welded surface, effectively preventing damage to the flexuous rubber tire 263 when the inspection roller 250 is rotated. The tire 263 is made of silicon rubber. The welded (cut) surface on which the tire 263 travels is recessed in an arc, but since the tire 263 is flexuous, inspection is performed with ease. Moreover, since the flash on the cut surface is removed, it is possible to utilize a flexuous tire.

The optical sensor 230 detects the width position of the projections 33, 33, and guides the device 200 to the center of the detected width. Especially, the width-direction position of the inspection roller 250 is disposed at a predetermined position.

The nondestructive inspection utilizes ultrasonic, and the inspection roller 250 is equipped with an ultrasonic probe 251. The probe 251 is equipped inside the roller 250. The probe 251 is mounted on a shaft 261 provide rotatably within a frame 260 suspended from the device 200. The probe 251 consists of a oscillator and a receiver, and is positioned to face downward. The probe 251 is set to constantly face downward by gravity. The tire 263 that comes into contact with the upper surface of the projections 33, 33 is fixed to wheels 265 disposed on both sides thereof. Both side surfaces of the tire 263 are pressed onto the wheels 265 by a hold metal 266. The wheel 265 is fixed to the shaft 261 via a bearing 268. The tire 263 is made of silicon. The probe 251 is arranged in the space defined by the tire 263 and wheels 265, 265, and a small amount of ethylene glycol is injected thereto as antifreeze. Reference 267 shows the opening through which the glycol is injected.

Figure 5:
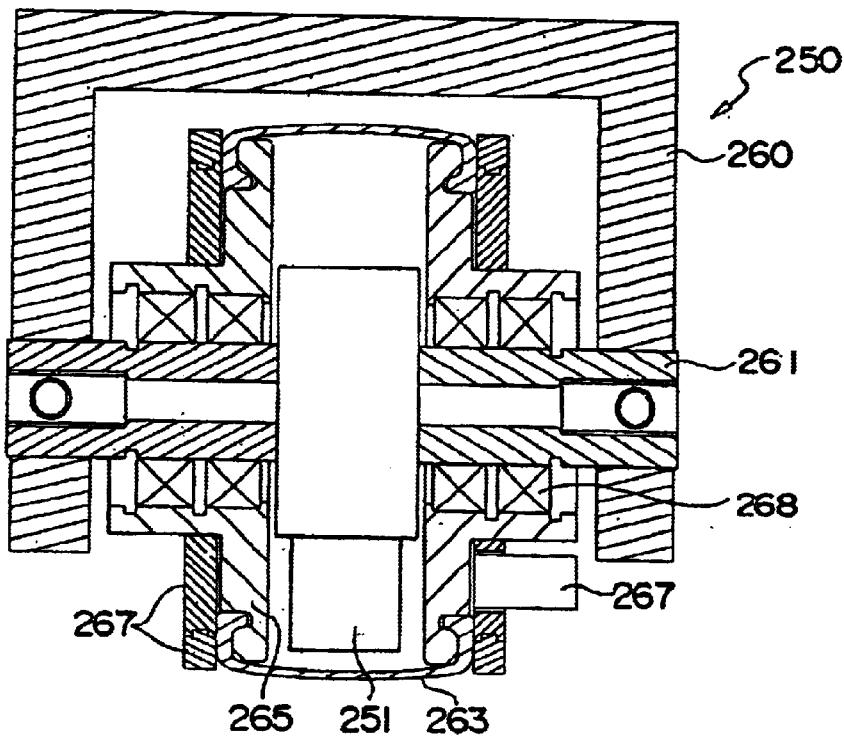
FIG. 5 is a vertical cross-sectional view showing the inspection roller of FIG. 1.
Figure 6:
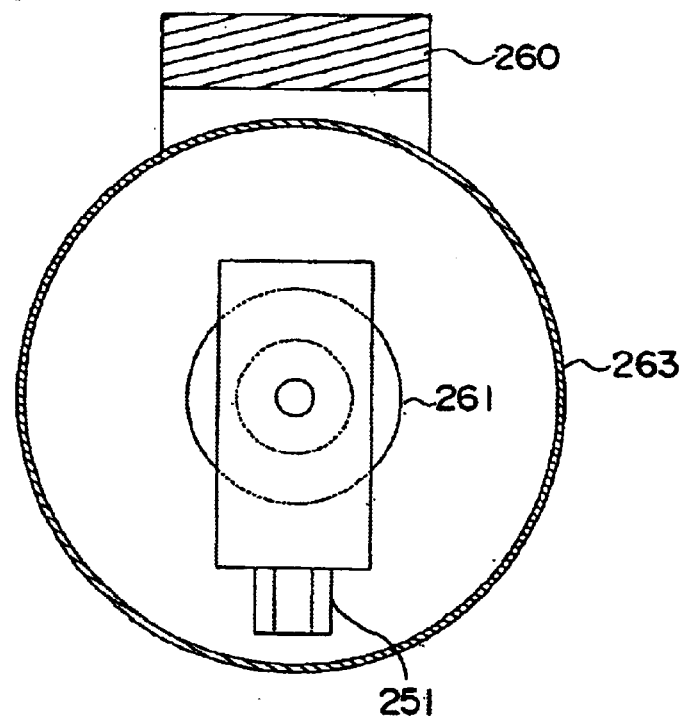
FIG. 6 is a central vertical cross-sectional view of FIG. 5.
Figure 7:
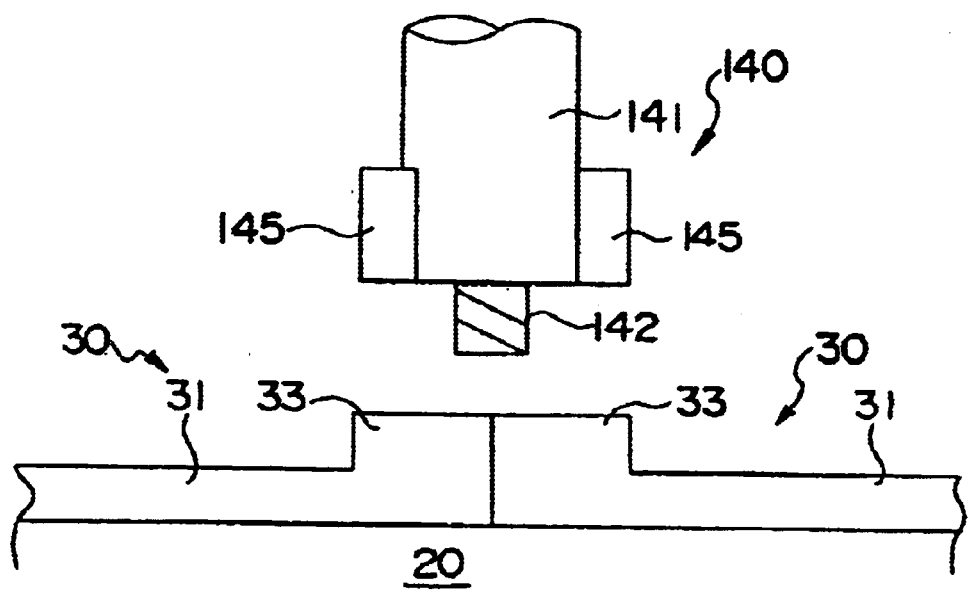
FIG. 7 is a vertical cross-sectional view showing the portion to be welded according to FIG. 1.

The lead wire of the probe 251 is taken out to the exterior through the inside of the shaft 261. In FIG. 5, the probe 251 should be arranged perpendicularly. When a vertical probe is used, defect can be inspected from above the projections 33, 33, and the width of the roller 250 can be minimized. If an oblique probe is used, the width of the roller must be increased, and it becomes difficult to inspect defect from above the projections 33, 33. The oscillator of the probe 251 utilizes a low frequency within the range of 4–5 MHz, the range set so as to enable easy transmission through the tire 263, and so as to correspond to the aluminum material forming the members 30, 30. Further, it is possible to improve the sensitivity of the probe by utilizing a composite oscillator.

Figure 8:
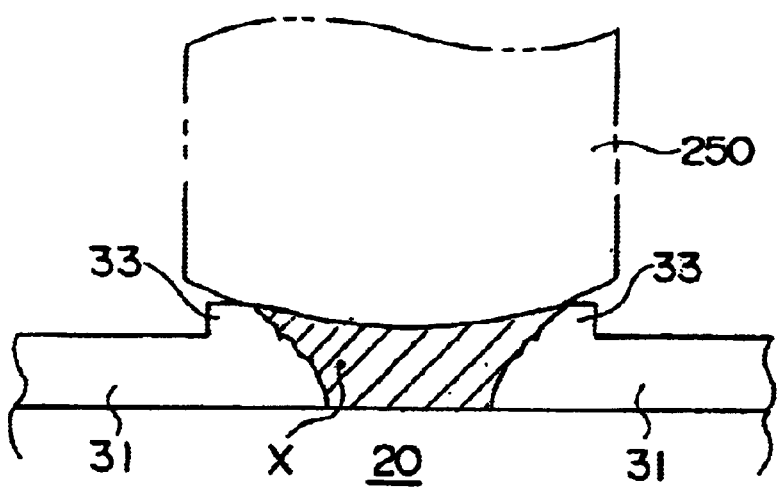
FIG. 8 is a vertical cross-sectional view showing the inspection of the joint portion according to FIG. 1.

In case of friction stir welding, it is possible to anticipate the position of the defect empirically. For example, as shown in FIG. 8, the position of defect X is biased toward one width direction from the center of the welded joint. This is determined by the rotation direction of the rotary tool 140. If the screw thread on the small-diameter portion 142 of the rotary tool 140 is a left-hand screw, and the rotary tool 140 is rotated in the right-hand direction, defect is likely to occur on the left side of the joint. Therefore, it is possible to set the probe 251 to inspect in detail the left side position where defect is likely to occur. FIG. 8 is a cross-sectional view showing a frame format of the joint portion. The hatching shows the stirred region. The probe 251 inspects the range within the stirred region where defect is anticipated.

A medium fluid supply device 240 is for applying the medium fluid on the upper surface of the projections 33, 33 on which the inspection roller 250 travels. The device 240 sprays the medium fluid onto the upper surface (welded surface) of the projections 33, 33. The medium fluid can be, for example, water. Since the central axis of the rotary tool 140 equipped with the blades 145 is tilted, the center portion of the cut surface is recessed. Therefore, the medium fluid is not likely to spread onto the plates 31, 31 even when the inspection roller 250 rolls on the cut surface. Therefore, the medium fluid can be collected easily by the suction device 280.

A marking device 270 is for applying paint to the position of defect when a defect is found in the friction stir weld joint. The existence of a defect is determined by a control unit based on the data gathered by the inspection roller 250. When defect is detected, the application is started from the point of defect, and the paint is continuously applied until the defect comes to an end. The paint should be easily recognized by visual observation, should easily adhere to aluminum alloy, should be quick-drying, and should not affect the aluminum alloy material. The marking device 270 can be, for example, an inkjet printer. The application is performed to one plate 31. Since the marking device 270 is positioned rearward from the inspection roller 250, the speed or time that the device 200 travels should be taken in to account, so as to correctly mark the position of defect.

The suction opening 280 for the medium liquid sucks up the medium liquid on the upper surface of the projections 33, 33 and the plates 31, 31 surrounding the projections. A soft brush is suspended from the lower end of the suction opening. The suction opening 280 is connected to a suction device.

When the friction stir welding device 100 starts friction stir welding and travels for a predetermined distance, the nondestructive inspection device 200 starts to follow the device 100 moving at the same speed as the device 100 and from the starting point of the friction stir welding. The brush of the device 200 removes the flash and the like on the surface being cut by the blades 145. The swarf generated therefrom is sucked up from the suction opening 225. The optical sensor 230 guides the inspection roller 250. The medium fluid is applied onto the surface through the supply opening 240, and the inspection roller 250 inspects the joint region. When defect is detected, a continuous line is printed on the plate 31 by an application device 270. The suction opening 280 sucks the medium fluid from the surface.

After the friction stir welding and inspection is performed as mentioned above, if a mark exists on the plate surface, mending is performed either at the location where the friction stir welding is performed or at another location to which the welded member is moved.

First, the welded portion being marked is cut from above, the cut reaching either the position of defect or to the other side of the plate. Next, the cut portion is welded by MIG or TIG. The welding is performed substantially to the height equal to the apex of the projections.

If the welded surface constitutes the exterior of a car body, or if by any other functional or esthetical reason the surface of the members must be smoothed, the projections 33, 33 (including the repaired portion) are removed by cutting, and the welded portion becomes substantially planar with the surface of the plates 31, 31.

According to the present embodiment, friction stir welding and the inspection of the weld joint can be performed. Since friction stir welding is performed under cold temperature, the welding and the inspection of the welded members can be performed substantially simultaneously by using conventional parts and materials.

The position of the nondestructive inspection device 200 will now be explained. Friction stir welding can be performed with relatively low heat in the range of approximately 450–500° C., since it only requires to plasticize the material around the joint. Therefore, when the friction stir welding is performed under a cool atmosphere, the temperature of the joint drops rapidly. Accordingly, nondestructive inspection can be performed by bringing the inspection device into contact with the joint portion. For example, upon friction stir welding the abutted portion between two aluminum alloy plates each having a thickness of approximately 3 mm, the temperature drops to approximately 75° C. when 100 seconds has passed after the welding (the speed of movement of the rotary tool: approx. 0.6 m/min). The temperature is measured at a position approximately 1.0 m away from the joint region. At such temperature, the nondestructive inspection device 200 can come into contact with the joint region and perform inspection.

The position on which the defect is marked can be the upper surface of the projection instead of the upper surface of the plate. In such case, the marking is performed rearward from the position where the medium liquid is collected.

When inspection for determining the depth of the defect is performed before the cutting process, the amount of cutting can be reduced. The depth of the defect is not clear by the inspection performed using the inspection roller 250. The depth of the defect is detected by moving the probe manually along the surface of the plate 31 where the defect position is marked and along the projection 33. If the side surface of the probe contacts the projection 33 when being moved, the probe can be moved linearly, and detection of the defect becomes easier.

The rotary axis of the rotary brush 220 can be arrange in the horizontal direction so as to blow the swarf rearward. The marking device 270 can either indicate the defect by a continuous line, or by an intermittent line. Moreover, the starting point of the defect can be shown by a mark different from a mark showing the ending point thereof, and marking of the areas therebetween can be omitted. Moreover, the medium liquid retrieving device is equipped with a roller that rolls on the joint surface and having on the outer circumference surface of said roller a porous member, and the rotary shaft of the roller is connected to the suction device.

The technical scope of the present invention is not restricted by the language used in the claims or the summary of the present invention, but is extended to the range in which a person skilled in the art can substitute based on the present disclosure.

According to the present invention, the weld joint can be inspected automatically for any defects, and especially, in friction stir welding, the welding and the inspection of the weld joint can be performed at the same time.

What is claimed is:

1. A nondestructive inspection method comprising:
    friction stir welding members to be welded by relatively moving a rotary tool against said members, thereby forming a welded portion;
    cutting and removing a part of said welded portion; and
    performing nondestructive inspection at a position rearward therefrom, wherein the nondestructive inspection is performed using a nondestructive inspection device, and wherein the rotary tool travels a distance and thereafter the nondestructive inspection device follows the rotary tool while the rotary tool continues the friction stir welding.

2. A nondestructive inspection method according to claim 1, further comprising marking the area of said member approximate the defect position when a defect is detected by said nondestructive inspection.

3. A nondestructive inspection method according to claim 1, further comprising removing swarfs from the cut surface after said cutting step, before performing said nondestructive inspection.

4. A nondestructive inspection method according to claim 1, wherein said cutting is performed by cutting the outer surface of said welded portion and its periphery to form a substantially flat surface, and then further cutting said cut surface using a brush.

5. A nondestructive inspection method according to claim 1, further comprising applying a medium fluid on said cut surface, and performing said nondestructive inspection at a position rearward from said application by moving a nondestructive inspection device on the surface where said fluid is applied.

6. A nondestructive inspection method according to claim 5, further comprising performing said nondestructive inspection, and sucking up and collecting said medium fluid at a position rearward therefrom.

7. A nondestructive inspection method according to claim 1, wherein said nondestructive inspection is performed by rotating a roller having a probe stored therein along said cut surface.

8. A nondestructive inspection method according to claim 1, wherein:
during said friction stir welding said members are positioned substantially flat;
said cutting is applied to said welded portion so that the cut surface has a recessed center portion;
a medium liquid is applied to said recessed center portion; and
the nondestructive inspection is performed by rotating a roller having a probe stored therein along the surface to which said medium liquid is applied.

9. A nondestructive inspection method according to claim 1, wherein
said nondestructive inspection is performed to inspect a predetermined portion in the width direction of the total width of the welded portion.

10. A nondestructive inspection method according to claim 1, wherein:
after performing said nondestructive inspection, a defect portion is marked, providing a marked portion, and the method further includes
performing nondestructive inspection of the marked portion so as to determine the depth of the defect;
cutting the marked portion to the depth of said defect; and
welding the cut portion.

11. A nondestructive inspection method according to claim 1, wherein:
during said friction stir welding said members are positioned substantially flat, with projections protruding upward at abutted ends of said members being abutted against one another, said friction stir welding being performed from the side provided with said projections;
said cutting includes cutting the apex side of said projections at said welded portion;
said nondestructive inspection is performed by rotating a roller having a probe stored therein;
after said nondestructive inspection, moving said probe to a marked portion so that said probe comes into contact with said projection, thereby nondestructively inspecting and detecting the depth of a defect;
cutting the marked portion to the depth of said defect, forming a cut portion; and
welding said cut portion.

12. A nondestructive inspection method according to claim 1, wherein the rotary tool moves along a joint between said members to perform the friction stir welding, the nondestructive inspection device following the rotary tool along the joint, and wherein the nondestructive inspection device moves at substantially a same speed as the rotary tool moving along the joint.

13. A nondestructive inspection method according to claim 12, wherein the nondestructive inspection device begins performing the nondestructive inspection at a starting point of the friction stir welding.

14. A nondestructive inspection method according to claim 1, wherein said nondestructive inspection device begins performing the nondestructive inspection at a starting point of said cutting.

15. A nondestructive inspection method according to claim 1, wherein said nondestructive inspection is performed using an inspection probe located within a roller that rolls along the welded portion.

16. A nondestructive inspection method according to claim 15, wherein said inspection probe is an ultrasonic probe inside the roller.

* * * * *